United States Patent
Donahue et al.

(10) Patent No.: US 9,651,465 B2
(45) Date of Patent: May 16, 2017

(54) GOLF-BALL COMPRESSION MEASUREMENT

(71) Applicant: GOLFTEK, LLC, Boston, MA (US)

(72) Inventors: John Donahue, Venice, FL (US); Matthew S. Kressy, Wellesley, MA (US); Paul Sabin, Needham, MA (US); Emily Batt, Merrimack, NH (US); Jeffrey Tyler, Superior, CO (US); Joseph E. Jalbert, Winchester, MA (US)

(73) Assignee: Golftek, LLC, Boston, MA (US)

( * ) Notice: Subject to any disclaimer, the term of this patent is extended or adjusted under 35 U.S.C. 154(b) by 0 days.

(21) Appl. No.: 15/081,209

(22) Filed: Mar. 25, 2016

(65) Prior Publication Data

US 2016/0238500 A1 Aug. 18, 2016

Related U.S. Application Data (63) Continuation-in-part of application No. PCT/US2014/057447, filed on Sep. 25, 2014.

(60) Provisional application No. 61/944,813, filed on Feb. 26, 2014, provisional application No. 61/882,051, filed on Sep. 25, 2013.

(51) Int. Cl.
*G01N 3/08* (2006.01)
*A63B 47/00* (2006.01)
*A63B 37/00* (2006.01)

(52) U.S. Cl.
CPC ............. *G01N 3/08* (2013.01); *A63B 47/008* (2013.01); *A63B 37/0003* (2013.01)

(58) Field of Classification Search
CPC .................................................... G01N 3/08

USPC ........................................................... 73/818
See application file for complete search history.

(56) References Cited

U.S. PATENT DOCUMENTS

| | | | | |
|---|---|---|---|---|
| 2,628,496 A * | 2/1953 | Wick | ................... | G01M 99/00 73/818 |
| 3,665,757 A * | 5/1972 | Hoag | ................... | A63B 47/008 33/501 |
| 4,555,028 A * | 11/1985 | Valehrach | ............ | A63B 47/008 209/599 |
| 5,031,710 A | 7/1991 | Parker | | |
| 6,196,073 B1 * | 3/2001 | Harding | ............... | A63B 47/008 73/862.381 |
| 6,755,085 B1 * | 6/2004 | Kazanjian | ................ | G01N 3/08 73/824 |
| 7,210,362 B2 * | 5/2007 | Tsutaya | .................... | G01G 3/14 73/862.627 |
| 9,383,271 B2 * | 7/2016 | Ojima | ....................... | G01L 1/22 |
| 2007/0163813 A1 | 7/2007 | Lewis | | |
| 2009/0120201 A1 * | 5/2009 | Mendoza | ................. | G01N 3/08 73/818 |
| 2012/0166106 A1 * | 6/2012 | Niemeyer, III | ...... | A63B 47/008 702/43 |

(Continued)

FOREIGN PATENT DOCUMENTS

JP 2000121522 A * 4/2000

*Primary Examiner* — Lisa Caputo
*Assistant Examiner* — Jamel Williams
(74) *Attorney, Agent, or Firm* — Occhiuti & Rohlicek LLP (57) ABSTRACT

A hand-held compression-tester for golf balls applies a biasing force to the golf-ball, loads it, and then releases the load so that only the biasing force remains. Based on the evolution of a loading curve during these intervals, the compression-tester estimates a compression value.

21 Claims, 12 Drawing Sheets

(56) References Cited

U.S. PATENT DOCUMENTS

2013/0263679 A1* 10/2013 Niemeyer, III ....... G01L 1/2231
73/862.636

* cited by examiner

GOLF-BALL COMPRESSION MEASUREMENT

RELATED APPLICATIONS

This is a continuation-in-part of international application PCT/US2014/057447, filed on Sep. 25, 2014, which claims the benefit of the Sep. 25, 2013 priority date of U.S. Provisional Application 61/882,051 and the Feb. 26, 2014 priority date of U.S. Provisional Application 61/944,813, the contents of all of which are herein incorporated by reference.

FIELD OF INVENTION

The invention generally relates to golf, and in particular, to golf-balls.

BACKGROUND

Golfing is a sport of increasing popularity among people of all ages. With the increase in popularity, golfers are continually striving to improve their game. Advancements in golf instruction, golf analytics, golf clubs, and golf-balls all aid this endeavor.

Proper golf-ball selection paired with a player's abilities can lead to improved golfing satisfaction and performance. An important property of a golf-ball is its compressions value.

Golf-ball manufacturers offer a range of golf-ball compression values. However, these compression values change with time. Such changes arise from many causes, including exposure to air, immersion in water, and temperature changes.

Golf-balls are frequently stored in golf bags that are kept in trunks of hot cars. In many cases, golf-balls are recovered from water hazards. As a result, variation of a golf-ball's compressibility can be considerable. This variation of compression can have adverse effects on a golf-ball's performance, and ultimately, on the golfer's game.

SUMMARY

The invention is based on the recognition that a more accurate for measurement of golf-ball compression is a dynamic measurement that evaluates the evolution of force during a measurement interval to estimate the compression value of a golf-ball. Because modern golf-balls are elastomers, the force compressing a ball to a fixed deflection varies over time. The present invention uses the varying force over the measuring interval to get an improved force value with only a modest deflection. Since only a modest deflection is needed, the forces required to test the golf-ball are lower. In fact, they are low enough to enable the device to be operated with one hand.

The present invention is directed to a golf-ball compression measurement apparatus. The apparatus includes an opening sized to receive a golf-ball. The opening is formed by a support structure and a beam. Upon receipt of the golf-ball, the golf-ball is compressed for the first time. The force exerted upon the beam over time by the compressed ball is proportional to a modulus, and thus the compression value. The force of the compressed golf-ball, which is different for different hardness of golf-balls, is measured by a strain gauge attached to the beam. A time series of force reading is stored in the computing device. This time series is then used as a basis for fitting a curve. Subsequent calculations then extract a single force that can be used as a basis for evaluating compression values. The ball is further compressed by a predetermined distance, again the force time series collected and a second curve is fit. The second single force point is chosen and knowing the deflections built into the devise a compression value is calculated and then displayed.

In effect, the measurement algorithm described above provides a dynamic model of the golf-ball as a spring and damper system. The benefit of compressing the golf-ball by a predetermined distance is that an accurate compression value can be calculated without having to measure the distance that the device has traveled.

In one aspect, the invention features a hand-held golf-ball compression meter. Such golf-ball compression meter includes a housing having a wall forming a circular opening on a first side thereof that has a circumference sized to receive a golf ball, an actuator configured to apply a first force to a golf ball, and an internal support structure that transmits a second force to a load beam coupled to a strain gauge. The compression meter also includes a computing system that receives, from the load beam, a load signal indicative of the second force. The computing system, obtains the load signal, a time series of force values and derives, from that time series, a golf-ball compression value and displays information indicative of that value on a display.

In some embodiments, the internal support structure comprises first and second golf-ball retainers that face each other and that define between them a space for positioning the golf-ball for measurement of the compression value thereof.

In other embodiments, the internal support structure comprises a compression pin positioned on a shim above the strain-gauge load beam.

Also among the embodiments are those in which the computing system causes the display to indicate the compression value using both textual information and graphic information.

In still other embodiments, the golf-ball compression meter comprises a communication interface for transmitting data to an external receiver.

Also among the embodiments are those that have a linkage that causes the compression meter to transition between a first state in which the compression meter applies a first force to the golf ball and a second state in which the compression meter applies a second force to the golf ball.

In another aspect, the invention features a method for measuring a compression value of a golf-ball by imposing a first force to cause the golf-ball to transition into a first loaded state, imposing a second force that, when added to the first force, causes the golf-ball to transition into a second state, releasing the second force, thereby permitting the golf-ball to transition back to the first state, measuring a time-varying load on the golf-ball during the transition back to the first state, and based at least in part on the time-varying load, estimating the compression value.

Practices of the invention include those in which measuring a time-varying load comprises causing the golf-ball to engage a load-beam of a strain-gauge, and providing an output of the strain-gauge to a processing system, those in which estimating the compression value comprises fitting a curve through the time-varying load and basing the estimate at least in part on a point on the fitted curve, and those in which estimating the compression value comprises fitting a curve through the time-varying load and basing the estimate at least in part on first and second points on the fitted curve.

In some practices, the first point is on a loading portion of the curve and the second point is on a recovery portion of the curve.

These and other features of the invention will be apparent from the following detailed description and the accompanying drawings, in which:

DETAILED DESCRIPTION

Figure 1:
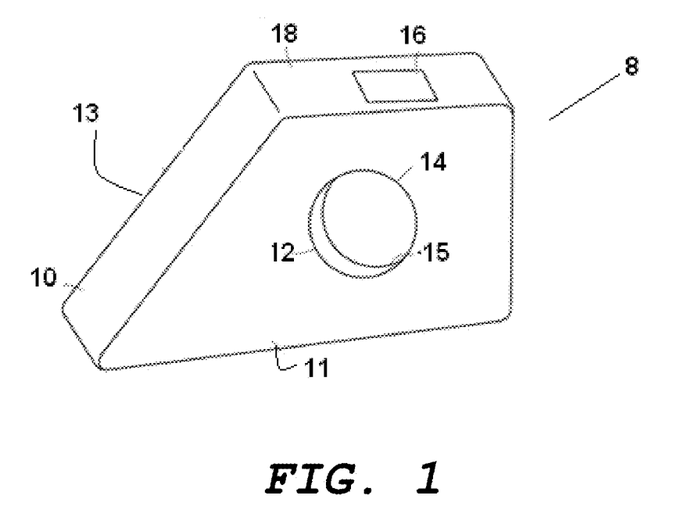
FIG. 1 is an isometric view of a golf-ball compression meter.

As shown in FIG. 1, an exemplary golf-ball compression meter 8 includes a housing 10 sized to be easily held by a player's hand. The housing 10 can made of any of a variety of materials, including metal, carbon, glass-fiber composites, plastic, or combinations thereof.

The housing 10 includes a display 16 on a top section 18 thereof. Examples of a display 16 include those that have a light-emitting diode display (LED) and those that have a liquid-crystal display (LCD).

A hole 12 extends through the housing 10 from a front side 11 to a rear side 13 thereof. The front 11 side has a front opening 14 adapted to receive a golf-ball 21. The rear side 13 has a corresponding rear opening 15 whose circumference is less than that of the front opening 14. The smaller circumference of the rear opening 15 prevents a golf-ball that has pressed through the front opening 14 from falling out of the housing 10 through the rear opening 15. The rear opening 15 also provides a convenient place for a user to push against a golf-ball to eject it.

The rear opening's smaller circumference is sized to enable proper positioning of a golf-ball 21 between an upper ball-retainer 20 and a lower ball-retainer 22. The upper ball-retainer 20 and the lower ball-retainer 22 are positioned above and below the front opening 14 respectively.

Figure 2:
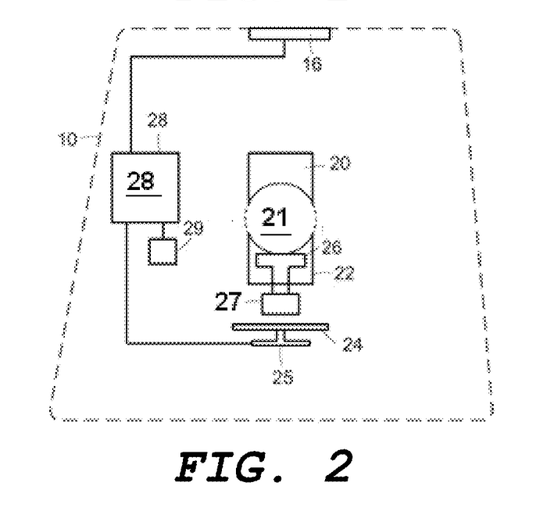
FIG. 2 shows internal components of the compression meter shown in FIG. 1.
Figure 3:
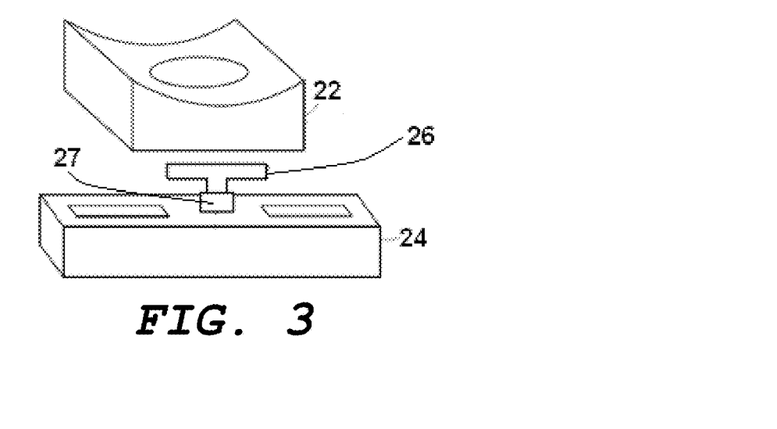
FIG. 3 shows a close-up of a portion of the internal components shown in FIG. 2.

Within the housing 10 is a load beam 24 fitted with a strain gauge 25, which can also be seen in more detail in FIG. 3. Also within the housing 10 is an internal support structure that provides an interface between the golf-ball and the load beam 24. In some embodiments, the internal support structure takes the form of a compression pin 26 that sits between the lower ball-retainer 22 and on a shim 27 supported by the load beam 24.

A computing system 28 links to the display 16 and to the load beam 24 using suitable wiring. A power supply 29 provides power for both the computing system 28 and the display 16. In one embodiment, the power supply 29 is a replaceable battery. In a typical embodiment, the computing system 28 includes a processor and a memory. In some embodiments, the computing system 28 is configured for data exchange. In these embodiments, the computing system 28 further includes a Universal Serial Bus (USB) port, Blue Tooth, and/or a WiFi adapter to facilitate data exchange. The exchanged data may then be used to track compression values of golf-balls from a particular manufacturer, from different manufacturers, and/or over periods of time. The compression value can also be provided to a second device, such as a smart phone, a GPS devices and/or another data receivers. As a result becomes possible to conveniently compression numbers of golf-balls from a particular manufacturer, from different manufacturers, and/or over periods of time.

In a preferred embodiment, the front section of the housing 10 has a 1.70" diameter opening that accepts a standard size golf-ball and a 1.375" opening on the rear section of the housing 10 that centers the golf-ball above the compression pin 26. The radius of the lower ball-retainer 22 is greater than that of the ball's diameter. This ensures that the internal support structure can transfer the entire compressive load to the load beam 24.

Figure 4:
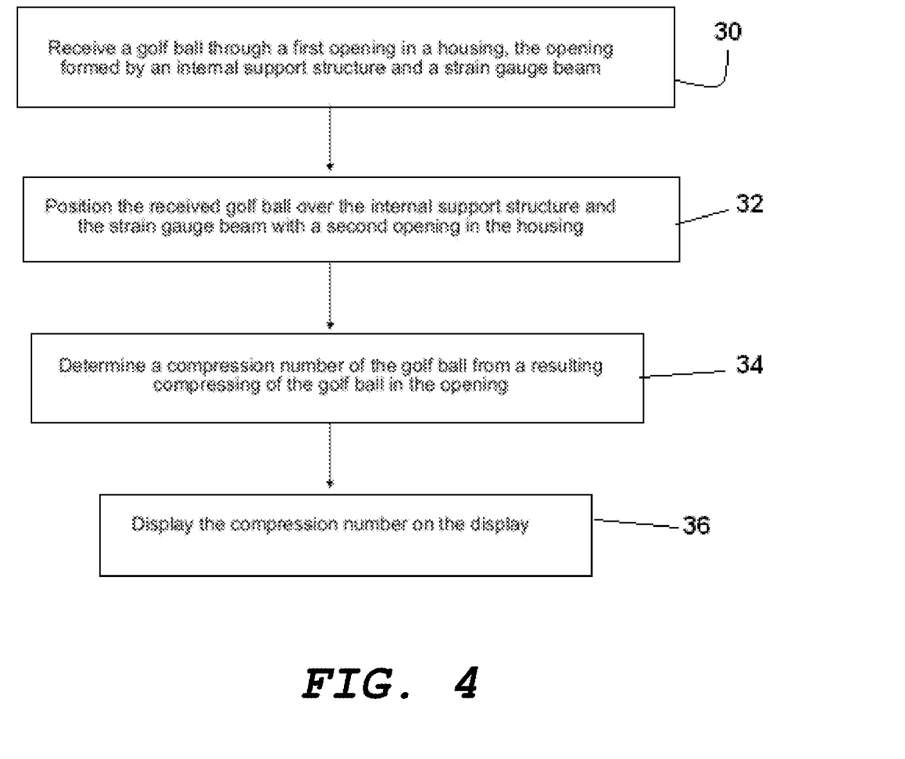
FIG. 4 shows a method for estimating compression value.

As shown in FIG. 4, a method of determining golf-ball compression includes receiving a golf-ball through the front opening 14 in the housing 10 so that the load beam 24 can support it (step 30), and positioning the received golf-ball over the internal support structure and the strain gauge load beam 24 with a second opening in the housing 10 (step 32). This is followed by determining a compression value of the golf-ball from a resulting compressing of the golf-ball in the first opening (step 34) and displaying the compression value on the display 16 (step 36).

In general, numeric compression values would vary noticeably depending on the orientation in which the ball is inserted into the compression meter 8. Therefore, to avoid confusion, it is preferable to quantize the compression value before display into one of several ranges and to simply identify range of values on the display 16. Thus, instead of displaying an actual numerical value, the display 16 displays a range in which the numerical value falls.

The display can communicate these ranges in any of several ways. For instance, the display can display words, such as "very soft," "soft," "medium," "firm" or "very firm."

In another embodiment, the display communicates the ranges as different colors. For example, black may indicate high compression value and a red may indicate lower compression.

In another embodiment, the display communicates the ranges using a gradient scale in which a number of illuminated bars indicate the ball's hardness.

Compression value is related to the ratio of compressive stress to compressive strain, which is sometimes referred to as the golf-ball's modulus. Compressive stress is the compressive force divided by the area of the sample. Compressive strain is the change in length from the uncompressed state to the compressed state divided by the uncompressed length.

The compression meter 8 operates by applying a first load to the golf-ball, thus causing it to transition into a biased state, adding a second load to the first load, thus causing the golf-ball to transition into a loaded state, and then releasing the second load, thus causing the golf-ball to revert back to its biased state.

Figure 5:
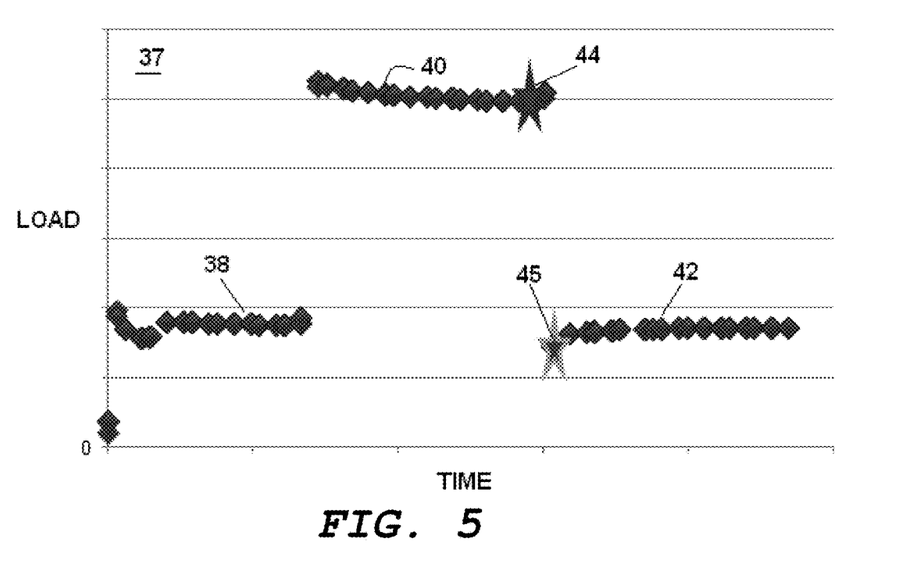
FIG. 5 shows a load curve.

Referring to FIG. 5, the foregoing procedure results in a load signal 37 having a biasing phase 38, a loading phase 40, and a recovery phase 42. The illustrated load signal 37 is obtained as a time series. Thus, in FIG. 5, the horizontal axis is time and the vertical axis is a measure of load. FIG. 5 thus shows a time series of load values.

The biasing phase 38 begins when the user inserts the golf-ball into the hole 12. This places the golf-ball into the biased state in which its diameter is reduced to the first diameter. As is apparent from FIG. 10, there is a relatively low load that settles into equilibrium.

The loading phase 40 begins when the user activates the actuator, thus squeezing the golf-ball into the loaded state. This results in a much higher load that likewise settles into equilibrium.

The recovery phase 42 begins when the user releases the force that caused the ball to be in the loaded state. As a result, the ball is free to revert to the biased state.

As can be seen in FIG. 5, curve fitting a times series promotes precision by smoothing out the irregularities in the many individual data points. The improved load-reading precision also allows lower forces to be applied to the golf-ball and more accurate compression values to be determined using the two fixed deflections. The lower forces, coupled with the mechanical advantage of the linkages discussed below enable one handed operation of the compression meter.

FIG. 5 also shows why using the force time series data from the unloading portion of the curve to select the low load point is advantageous. In the initial loading of the ball in the very first fraction of a second that the ball is compressed, it goes through an initial reduction in the required force and then very shortly the force value increases. At that point the force decays slightly before starting to increase again. Upon increasing the force to the higher level, the force again decays a small amount. One embodiment is to use the force value at the end of the high load time series before it starts to increase. This embodiment uses the beginning of the unloading low load force time series as the selected low force as this curve is well behaved without the abrupt changes in force seen during the initial low loading.

In operation, the user presses the golf-ball by hand through the front opening 14 so that it rests on top of the compression pin 26, which itself is on the shim 27 supported by the strain gauge's load beam 24. This compresses the golf-ball in the process, thus placing it in its biased state. The biased golf-ball now exerts a force on the load beam 24. This force is proportional to the modulus of the golf-ball, and thus the compression value.

The load beam 24 provides the strain gauge 25 with a basis for measuring this force. The strain gauge 25 provides its measurement to the computing system 28, which calculates an appropriate value to show on the display 16.

Preferably, the golf-ball is compressed with minimal or no rotation, as would occur if one were using a screw or a similar device.

The measuring system uses a strain gauge 25 to measure the force used to compress the golf-ball. The internal support structure controls golf-ball placement within the housing 10 and prevents unnecessary golf-ball movement.

Figure 6:
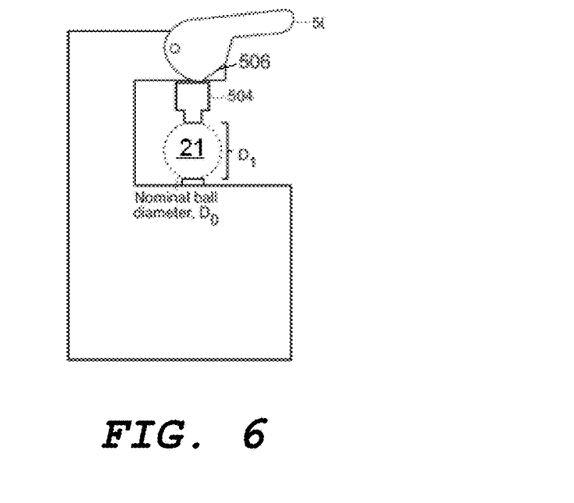
FIG. 6 shows an actuator in the disengaged position

FIG. 6 shows an embodiment in which an actuator comprises a lever arm 502 having a cam 506 on a distal end thereof. When the user moves the lever arm 502, the cam 506 causes an upper compression pin 504 to exert a first force on the golf-ball. This causes the golf-ball to transition into its loaded state.

The golf-ball rests on a lower compression pin 26, which rests on a shim 27 that ultimately transmits a second force to the load beam 24 of the strain gauge 25. The strain gauge 25 provides a load signal 37 indicative of the load on the golf-ball to the computing system 28.

In FIG. 6, the lever arm 502 is in a disengaged position. In this position, the golf-ball 21 is biased as a result of being within a space that has a first diameter D1 that is slightly smaller than the nominal diameter D0 of the golf-ball 21. This places the golf-ball 21 in an initial state in which it experiences a load associated with the difference between the nominal diameter and the first diameter. By subjecting each golf-ball to a constant bias prior to the actual measurement of compression value, the compression meter 8 tends to eliminate errors caused by variations in golf-balls. This tends to promote accuracy.

Figure 7:
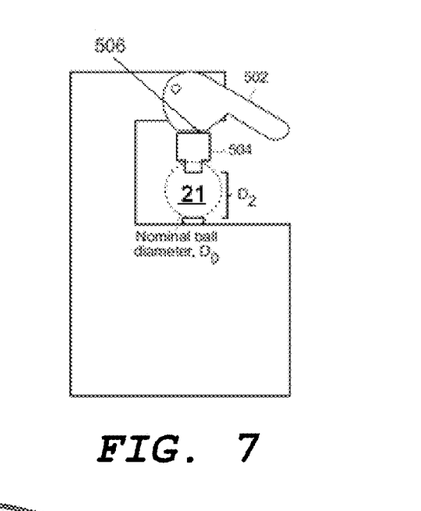
FIG. 7 shows an actuator in the engaged position

In FIG. 7, the lever arm 502 has been moved into an engaged position. This results in application of a force that causes the golf-ball 21 to deform until it reaches a second diameter D2. At this point, the golf-ball 21 is in its loaded state. This force is maintained until the golf-ball 21 reaches an equilibrium final state. When this force is released, the golf-ball 21 begins the process of recovery to its biased state.

During the loading phase 40, the lever arm 502 deforms the golf-ball. This requires work, which is manifested in an increase in the internal energy of the golf-ball 21. In the recovery portion, the golf-ball 21 releases the internal energy as it recovers its original shape. The rate at which the golf-ball 21 releases this internal energy provides information on its compression value. From the point of view of the computing system 28, the rate at which this energy is released can be derived by analysis of a time series showing the evolution of this load signal 37 over time. This time series thus contains important information concerning the properties of the golf-ball 21.

Golf-balls are typically viscoelastic. This means that when the golf-ball is compressed to a fixed distance, its load signal 37 will have an initial maximum load followed by decay over time. To estimate the load, the computing system 28 fits an equation to the decay curve. Suitable equations reply on a log fit or an exponential fit.

After having estimated an analytic representation of the fitting function, the computing system 28 can either extrapolate to shorter or longer than recorded times (abscissa values) or rely on an abscissa associated with a fixed ordinate as a basis for measurement. This ordinate represents a constant offset from the instant that the initial load is applied. The offset, in the case of the loading phase, should be long enough to allow the golf-ball to reach equilibrium. A suitable offset in many cases is one second after the maximum load. The offset in the case of the recovering bias state is chosen to be very short. Preferably, the offset is much less than 1 second.

FIG. 5 shows first and second points 44, 45 that are used as a basis for estimating compression value. The first point 44 corresponds to a higher load and the second point 45. In the embodiment describe herein, the time corresponding to the second point 45 comes after the time corresponding to the first point 44. This is believed to provide a more accurate estimate. However, in principle it is also possible for the second point 45 to come before the first point 44.

Figure 8:
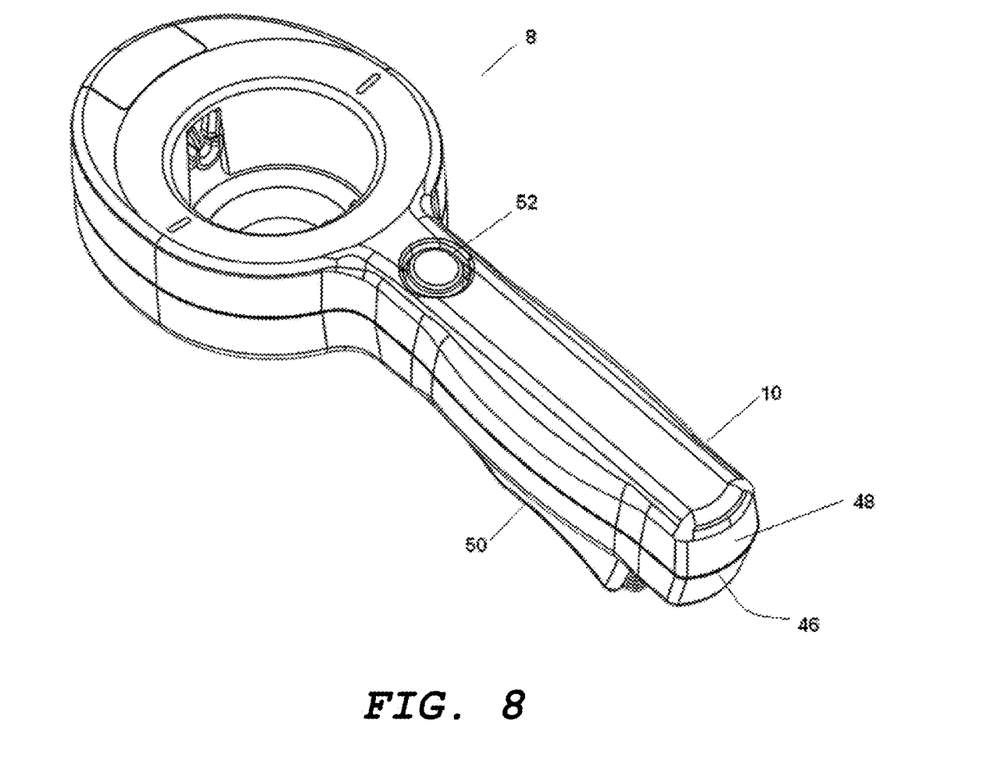
FIG. 8 shows an isometric view of an alternative embodiment of a golf-ball compression meter.

FIG. 8 is an isometric view of a compression meter 8 having a housing 10 consisting of a ventral half 46 and a dorsal half 48 joined together. A trigger 50 on the ventral half 46 causes a golf-ball to transition from its biased state to its loaded state. A release button 52 on the dorsal half 48 causes the golf-ball to transition from its loaded state back to the biased state.

Figure 9:
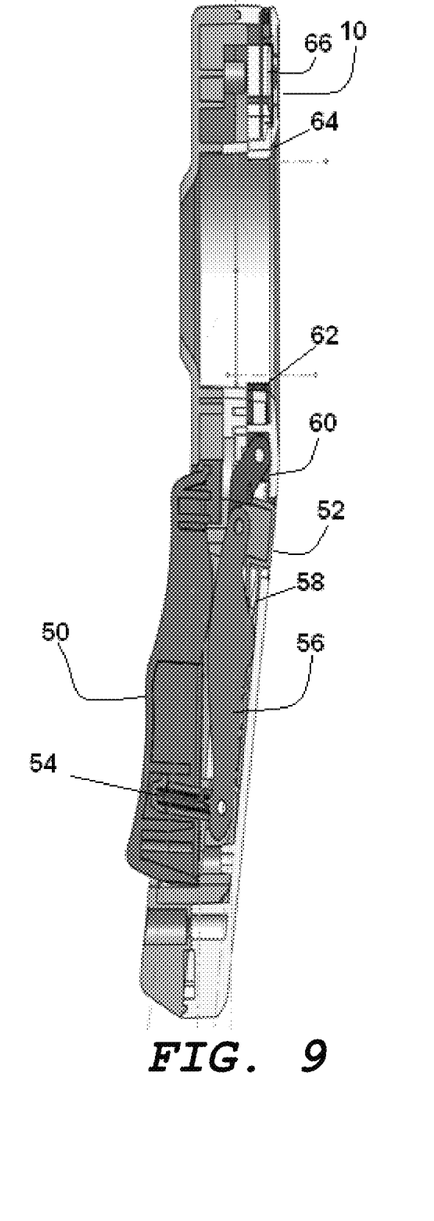
FIG. 9 is a cross-section of the compression meter shown in FIG. 8.

FIG. 9 shows a cross-section of the housing 10 in FIG. 8 in which one can see that when a user squeezes the trigger 50, it compresses a first spring 54 and moves a first linkage, 56 into engaged position. This, in turn, compresses a leaf spring and a second spring 58. This causes part of the release button 52 to protrude out of the housing 10 so that the user will later be able to cause the golf-ball to transition back to the biased state.

The first linkage 56 moves a second linkage 60 into an engaged position. The second linkage 60 then moves a lower anvil 62 into its engaged position. The lower anvil 62 exerts additional force onto the golf-ball, thus placing it into its loaded state. The increase force exerted on the golf-ball is transmitted to an upper anvil 64 and eventually conveyed to a load module 66 that includes the strain gauge 25 and other components described in connection with FIG. 1-3 for measuring load. The anvils 62, 64 can take on a variety of forms, such as a diamond form, a hexagonal form, or an octagonal form.

Once the user has pressed the trigger 50, the processing system 28 goes to work recording the load signal 37. A short time thereafter, the display 16 will instruct the user to press the release button 52.

Pressing the release button 52 ends the loading phase 40 by pushing the first and second linkages 56, 60 back to the unengaged position and drawing the lower anvil 62 back to the position it was in during the biasing phase 38. It also returns the trigger 50 back to its original position protruding out from the housing 10 with some help from the first spring 54. The processor 28 then continues to record the load signal 37, selects the representative high and low force values at the first and second ordinates 44, 45, and calculates and displays information indicative of the compression value on the display 16.

The first and second linkages 56, 60 allow multiple diameters to be measured. The opening 12 is slightly smaller than the industry-standard nominal golf-ball diameter of 1.68 inches. Inserting the golf-ball 21 into the opening 12 places the golf ball into a ball chamber that is slightly too small for the golf ball. This compresses the ball and exerts a bias force on the strain gauge 26 beneath the golf-ball 21. By engaging the linkages 56, 60 to a fixed stop, the user reduces size of the ball chamber. This further compresses the golf-ball 21. Since the two sizes of the ball chamber have been pre-defined, the computing system 28 can calculate the difference between F1 and F2 to yield the slope of the load deflection curve. The computing system 28 converts this value to a rating familiar to golfers and displays it on the display 16.

Figure 10:
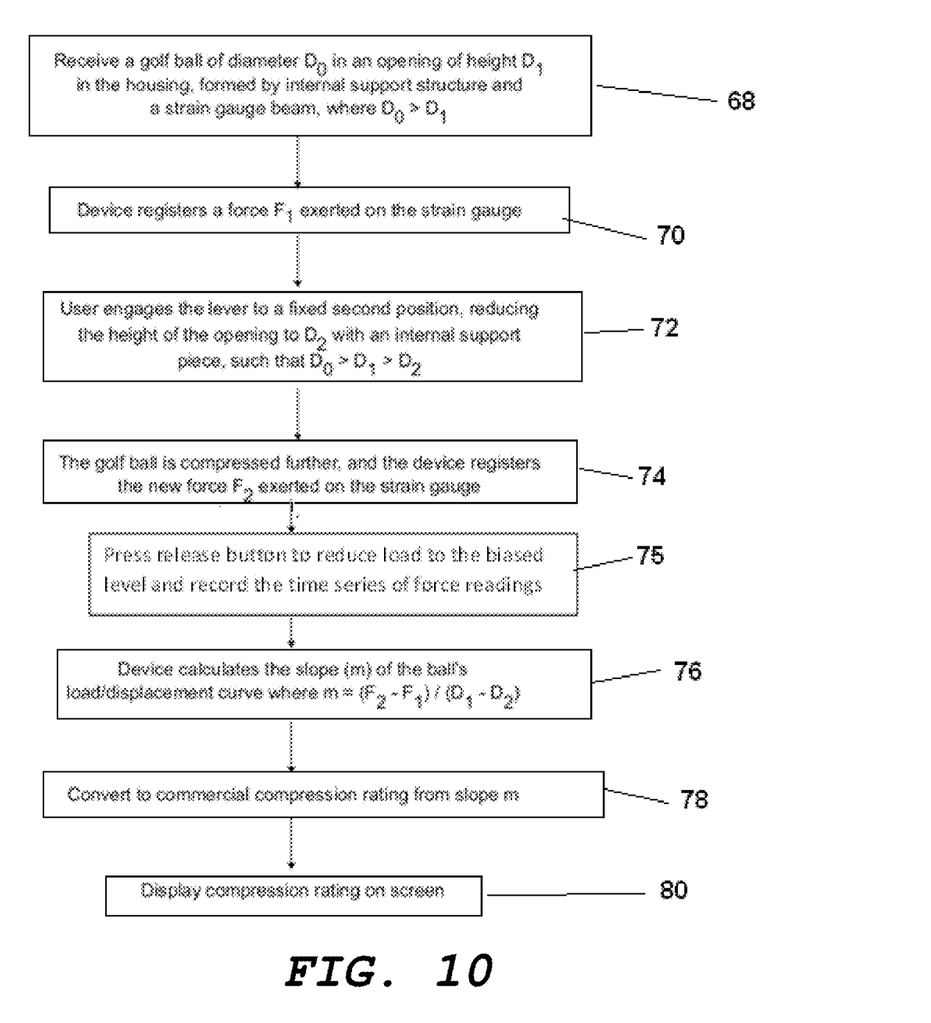
FIG. 10 is a flow-chart of a method for calculating a compression value using the compression meter in FIG. 8.

Referring now to FIG. 10 the two-step method carried out by the computing system 28 includes receiving a golf ball into the ball chamber (step 68) so that the strain gauge 25 measures a bias force (step 70). The user then squeezes the trigger, thus shrinking the ball chamber (step 72) and increasing the loading force significantly (step 74). After a brief interval, display 16 prompts the user to press the release button. In response, the user presses the release button (step 75). The processor then records a time series as the load signal 37 transitions from the loading phase 40 to the recovery phase 42, where the ball 21 again experiences the same initial bias force F1.

Based on the recorded time series, the computing system 28 then calculates a slope based on the points identified by the first and second ordinates 44, 45 (step 76) and the fixed deflection. The computing system 28 then converts this slope to the corresponding commercial compression rating (step 78) and displays information indicative of the compression rating on the display 16 (step 80).

In determining compression value obtained from two points along the load signal 37, the compression meter 8 calculates a slope, converts it into a form that would be familiar to golfers, and shows the result on the display 16. An advantage of this method is that one can determined a golf-ball's compression without having to know its initial diameter. This eliminates error caused by manufacturing variations, as well as size changes resulting from environmental variables, such as temperature. The use of two known positions removes the requirement for measuring displacement. This results in a particularly simple compression meter 8 that avoids the use of complex devices such as linear encoders to determine displacement.

By obtaining two compression measurements without removing the ball or adjusting its position, the data are collected over the same surface features, thereby negating any dimple effects. Furthermore, when D1 and D2 are appropriately small, the ball's load/displacement characteristics are comfortably within the linear region of the curve. Therefore, the device calculates the compression rating in a regime below a golf club strike, producing an accurate and valuable measurement for the golfer, without damaging the ball.

Figure 11:
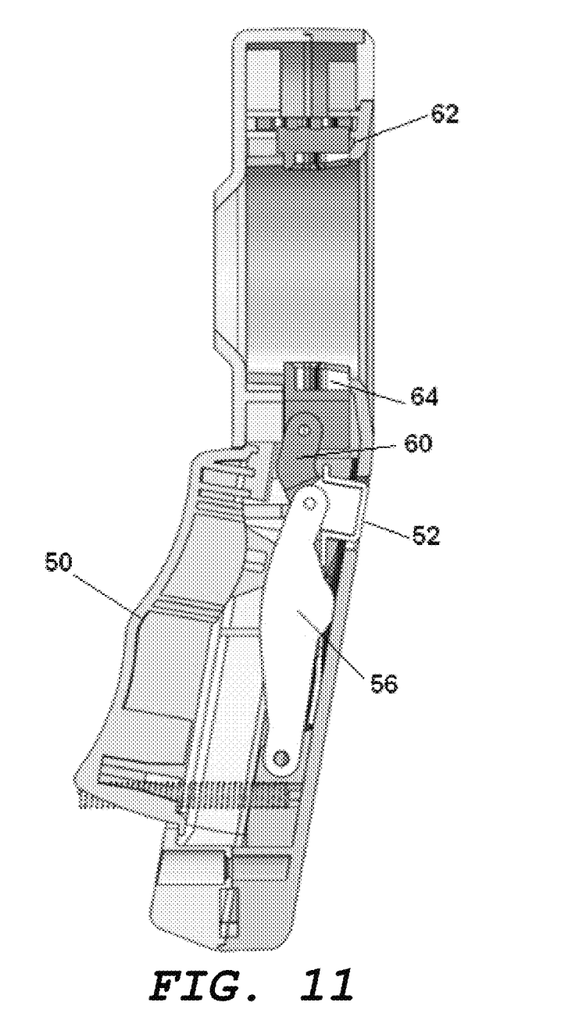
FIG. 11 shows a cross-section of a housing prior to the loading phase shown in FIG. 5.

FIG. 11 shows a cross-section of the housing 10 when the compression meter 8 is in the disengaged position of the biasing phase 38, in which the linkages 56, 60 are positioned to make the low force measurements. To increase the force, the user would grip the device in one hand and use their fingers to squeeze the trigger 50.

Figure 12:
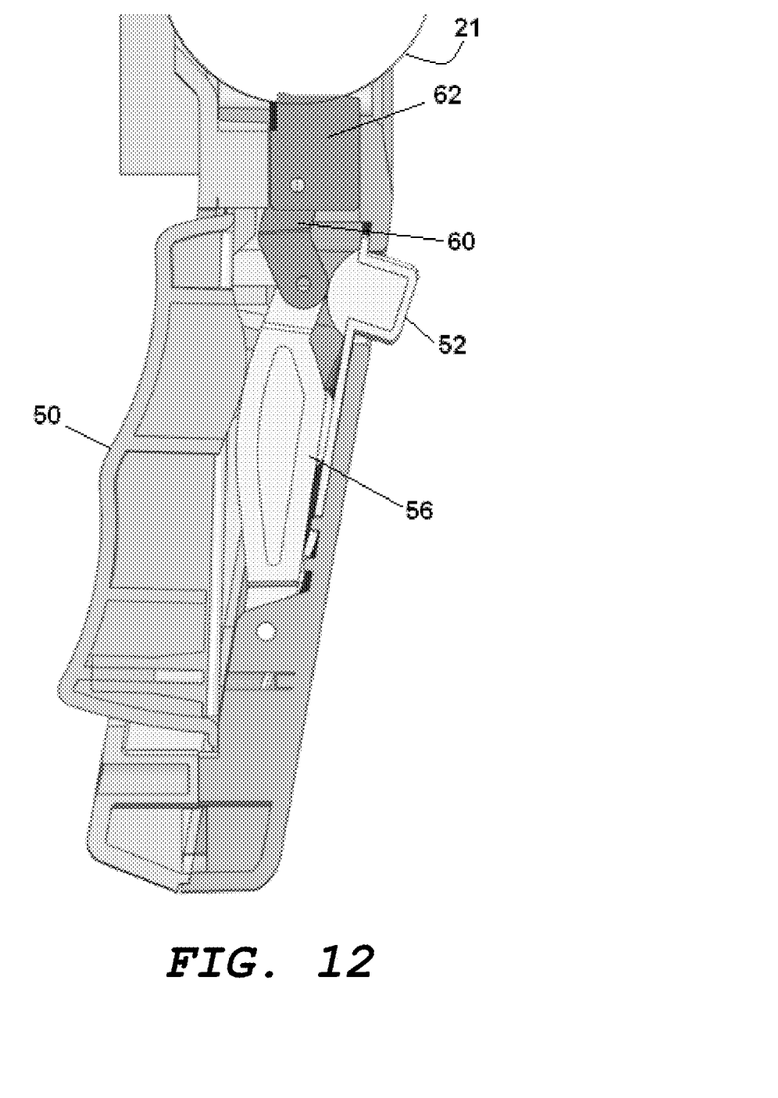
FIG. 12 shows a cross-section of the housing in the loading phase shown in FIG. 5.

FIG. 12 shows a cross-section of the compression meter 8 in the loading phase 40 just after the trigger 50 has been squeezed. The trigger 50 provides mechanical advantage and applies a greater force on the first linkage 56 to rotate the second linkage 60. The second linkage 60 urges the release button 52 out of the housing 10. The final part of the linkage is the lower anvil 62 which is attached to a distal end of the second linkage 60. In the loading phase 40, the lower anvil 62 moves into a position in which it further compresses the golf-ball 21.

Figure 13:
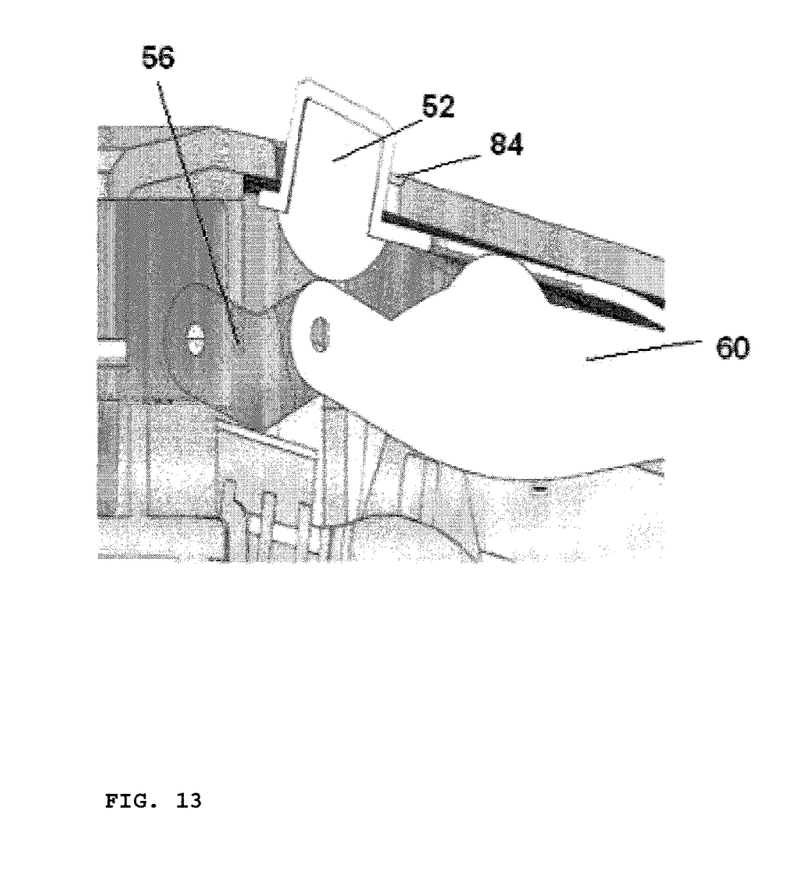
FIG. 13 shows the rubber or elastomeric ring that surrounds the release button.

As shown in FIG. 13, a thin ring 84 of rubber or elastomeric material surrounds the release button 52. This ring 84 provides cushioning when the trigger action engages the linkages and snaps the release button 52 into its out position. It also dampens a great deal of objectionable noise.

Figure 14:
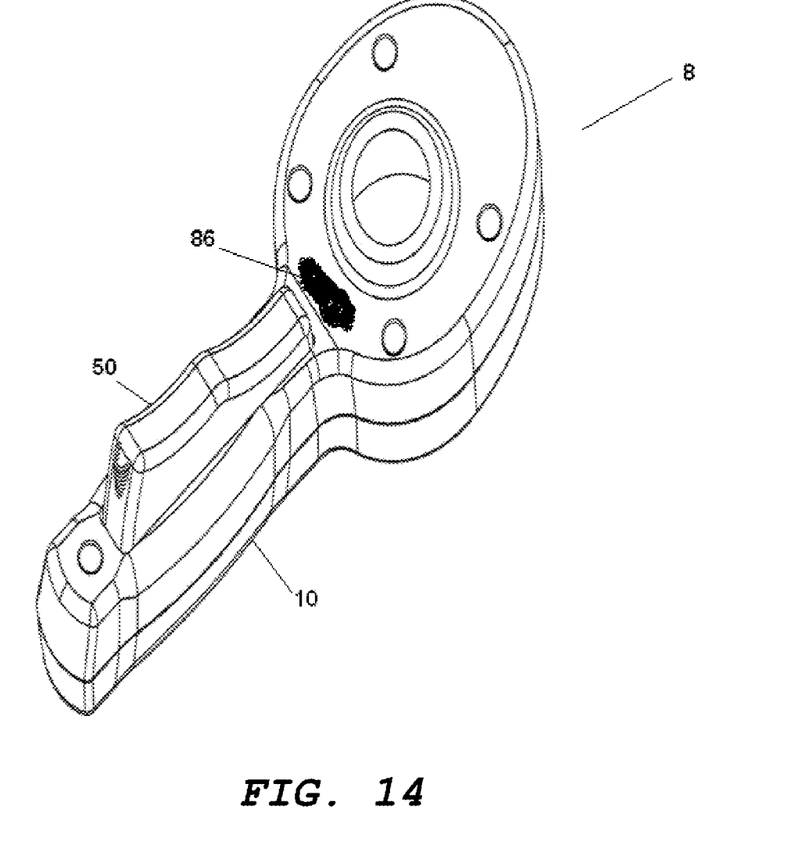
FIG. 14 shows a textured region that enhances the grip and identifies the finger position that facilitates pressing the release button.

As shown in FIG. 14, a textured region 86 distal to the trigger 50 enhances the grip guides the user to the most advantageous location to grip the compression meter 8 to press the release button.

Figure 15:
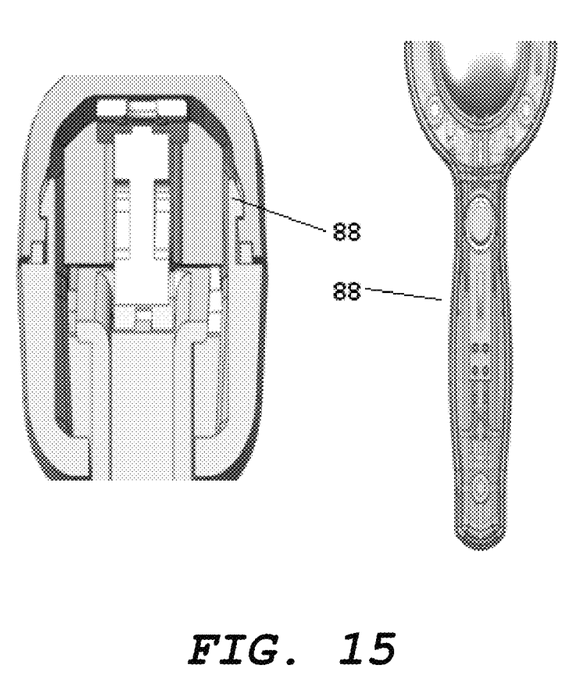
FIG. 15 shows details of snap clips that provide support in keeping the two halves of the housing together under load.

This compression meter 8 is a precision measuring apparatus. It is therefore important to maintain the integrity of the housing 10 while simultaneously keeping weight to a practical minimum. FIG. 15 shows details of the design for snap clips 88 that provide additional support in keeping the dorsal and ventral halves 46, 48 of the housing 10 together under load.

In practice, measured compression values are a function of which axis on the ball one applies the compressive force.

Thus, if one were to measure a ball's compression value, and to then remove the ball, rotate it ninety degrees, and re-insert the ball, the second compression value might well be different from the first.

Figure 16:
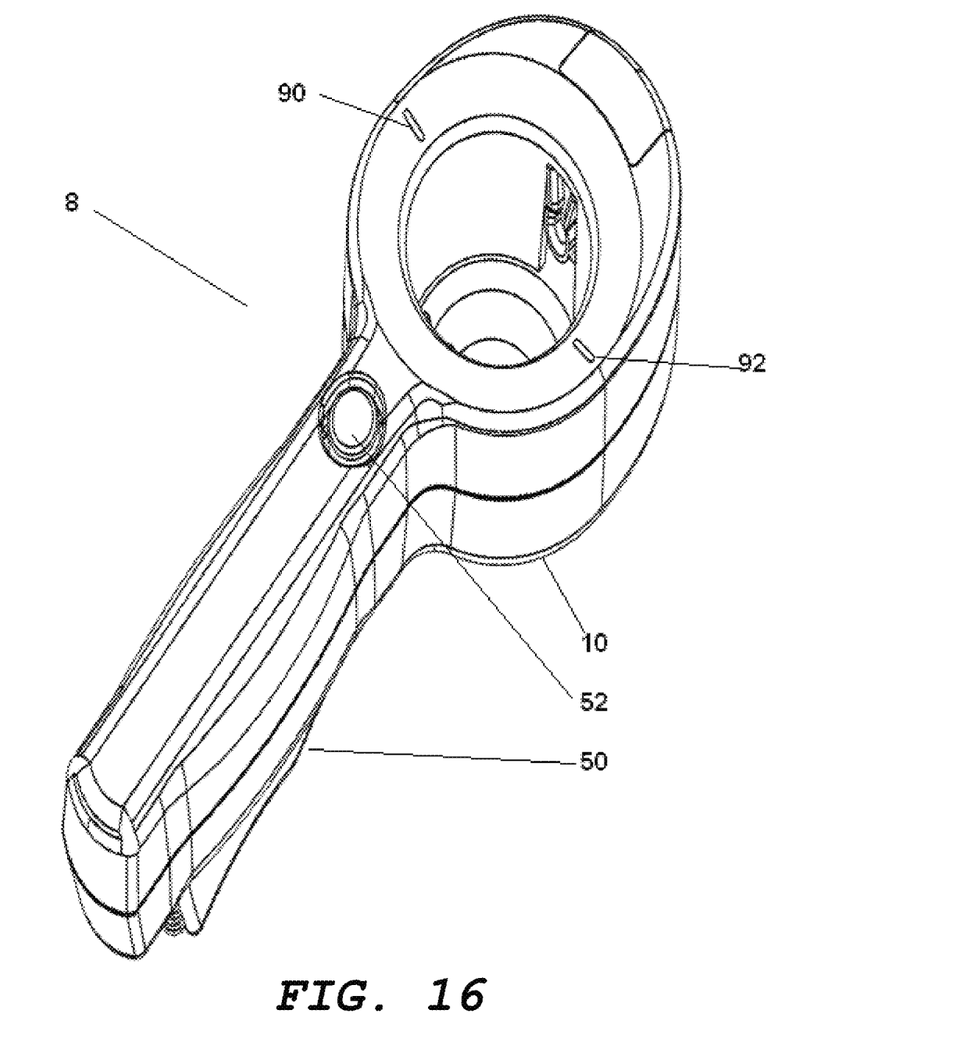
FIG. 16 shows fiducials used to visually align a golf-ball for insertion into the compression meter.

In recognition of the foregoing phenomenon, when inserting the ball, it is useful to orient the ball in the same manner as it will be oriented when being struck by a club after the measurement. This will ensure that the compression rating accurately represents the feel the golfer can expect upon contact. Some balls have as much as 10% difference between the compression value on one orthogonal axis compared to another. FIG. 16 shows fiducials 90, 92 that can be used to visually align a golf-ball for insertion into the compression meter 8.

Other mechanisms can be used to compress the golf-ball. For example, in one embodiment, a closing motion of a clamshell exerts a compression force on the golf-ball.

A compression meter 8 as described herein thus provides a convenient way to measure the compression of a golf-ball that is also small enough to fit into a golf bag and easy to use. It provides at least a reasonable estimate of that value by measuring deflection or strain and the force required to achieve that deflection.

Having described the invention, and a preferred embodiment thereof, what we claim as new, and secured by Letters Patent is:

1. An apparatus comprising a golf-ball compression meter comprising a head and a handle, wherein said head comprises an opening and a support structure, wherein said opening has an opening diameter that is smaller than a golf ball diameter, wherein a golf ball inserted into the opening and supported by said support structure experiences a biasing force corresponding to a difference between said opening diameter and said golf ball diameter, wherein said handle comprises a trigger and a release button, wherein said trigger is coupled to a linkage that causes application of a loading force in excess of said biasing force, wherein said release button, when actuated, releases said loading force, thereby causing said golf ball to experience only said biasing force, said golf ball compression meter further comprising a computer system coupled to said support structure, said computer system being configured to record a time series from a load signal that is generated as a result of squeezing said trigger and releasing said release button, and wherein said computer system is configured to estimate a compression value based on a slope of a portion of said time series and to communicate information indicative of said compression value.

2. The apparatus of claim 1, wherein said computer system is further configured to estimate said compression value based on first and second measurements of said load signal, wherein said first measurement is obtained at a first point in time and wherein said second measurement is obtained at a second point in time, wherein said first measurement corresponds to a response of said golf ball to said biasing force, and wherein said second measurement corresponds to a response of said golf ball to said loading force.

3. The apparatus of claim 2, wherein said second measurement occurs before said first measurement.

4. The apparatus of claim 1, wherein said computer system is configured to display information indicative of a range of compression values into which an estimate of a compression value of said golf ball falls.

5. The apparatus of claim 1, wherein said support structure comprises a loading beam and a strain gauge coupled to said loading beam, wherein said strain gauge provides said load signal to said computer system.

6. The apparatus of claim 1, wherein said support structure comprises an upper and lower ball-retainer for engaging said golf ball.

7. The apparatus of claim 1, further comprising an elastomeric ring around said release button.

8. The apparatus of claim 1, further comprising a textured region on at least one of said head and said handle.

9. The apparatus of claim 1, further comprising a compression pin coupled to said trigger such that squeezing said trigger causes said compression pin to press against said golf ball.

10. The apparatus of claim 1, further comprising a communication interface for transmitting data to an external receiver.

11. The apparatus of claim 1, wherein said linkage causes a transition between a first state in which a first force is applied to said golf ball and a second state in which a second force is applied to said golf ball.

12. The apparatus of claim 1, further comprising a display, wherein said information is communicated to said display.

13. The apparatus of claim 1, wherein said head further comprises a fiducial to assist in alignment of said golf ball when inserting said golf ball into said head.

14. The apparatus of claim 1, wherein said support structure comprises first and second golf-ball retainers that face each other and that define between them a space for positioning said golf-ball for measurement of said compression value thereof.

15. The apparatus of claim 1, wherein said support structure comprises a strain-gauge load beam, a shim, and a compression pin, wherein said compression pin is positioned on said shim above said strain-gauge load beam.

16. The apparatus of claim 1, further comprising a display, wherein said display is configured to provide a graphical display of said information.

17. The apparatus of claim 1, wherein said compression meter is configured to measure a time-varying load on said golf-ball during said transition of said golf ball from a second state, in which said golf ball was subjected to a combination of said biasing force and said loading force, to a first state, in which said golf ball is subjected only to said biasing force, and wherein said computing system is configured to estimate said compression value based at least in part on said time-varying load.

18. The apparatus of claim 1, wherein said support structure comprises a loading beam and a strain gauge coupled to said loading beam, wherein said compression meter is configured to cause said golf-ball to engage said loading-beam, and wherein said processing system is connected to said strain gauge to receive an output from said strain gauge.

19. The apparatus of claim 17, wherein said computer system is configured to fit a curve through said time-varying load and to base an estimate of said compression value at least in part on a point on said fitted curve.

20. The apparatus of claim 1, wherein said computer system is configured to fit a curve through said time-varying load and to base an estimate of said compression value at least in part on first and second points on said fitted curve.

21. The apparatus of claim 1, wherein said computer system is configured to fit a curve through said time-varying load and to base an estimate of said compression value at least in part on a point that is on a portion of said fitted curve during which a load is being applied to said golf ball and on a point that is on a portion of said fitted curve during which said golf ball is recovering from having been loaded.

* * * * *